United States Patent [19]

Zajic et al.

[11] 4,028,182
[45] June 7, 1977

[54] MICROBIOLOGICAL SYNTHESIS OF PROTEINACEOUS MATERIAL EMPLOYING NORMALLY GASEOUS HYDROCARBON SUBSTRATE AND THE PRODUCTS THEREOF

[75] Inventors: James E. Zajic, London; Bohumil Volesky, St. Lambert, both of Canada

[73] Assignee: Canadian Patents and Development Limited, Ottawa, Canada

[22] Filed: Mar. 26, 1975

[21] Appl. No.: 562,085

Related U.S. Application Data

[63] Continuation-in-part of Ser. No. 316,151, Nov. 18, 1972, abandoned, which is a continuation-in-part of Ser. No. 55,810, July 17, 1970, abandoned.

[52] U.S. Cl. .............................. 195/28 R; 195/81; 195/96; 195/111
[51] Int. Cl.² ............................................. C12B 1/00
[58] Field of Search ............ 195/28 R, 81, 111, 96, 195/115, 3 H

[56] References Cited

UNITED STATES PATENTS

| | | | |
|---|---|---|---|
| 2,822,319 | 2/1958 | Monud | 195/115 |
| 2,951,017 | 8/1960 | Speedie et al. | 195/115 |
| 3,151,038 | 9/1964 | Gray | 195/81 X |
| 3,297,545 | 1/1967 | Zajic et al. | 195/28 R |
| 3,384,491 | 5/1968 | Guenther et al. | 195/28 R |
| 3,418,208 | 12/1968 | Coty | 195/28 R |
| 3,635,796 | 1/1972 | Imada et al. | 195/28 R |
| 3,672,953 | 6/1972 | Coty et al. | 195/115 |
| 3,677,895 | 7/1972 | Hashimoto | 195/28 R |

*Primary Examiner*—R. B. Penland
*Attorney, Agent, or Firm*—Hirons & Rogers

[57] ABSTRACT

A new process for cultivating selected cultures involves initially removing broth at a first rate from a fermentation and replacing it with supporting medium, the replacement rate thereafter being increased to remove cultures of lower growth rate than the selected culture. A new process for the microbiological synthesis of protein-containing material by an aerobic fermentation in a supporting medium uses a normally gaseous hydrocarbon substrate selected from nethane, ethane, propane and butane and a protein-producing fungus of *graphium* species. It has not been known hitherto for such syntheses to be possible with a fungus. The said substrate may be natural gas.

18 Claims, 4 Drawing Figures

MICROBIOLOGICAL SYNTHESIS OF PROTEINACEOUS MATERIAL EMPLOYING NORMALLY GASEOUS HYDROCARBON SUBSTRATE AND THE PRODUCTS THEREOF

CROSS-REFERENCE TO RELATED APPLICATIONS

This application is a continuation-in-part of our application Ser. No. 316,151, filed Nov. 18, 1972 now abandoned, which in turn was a continuation-in-part of our application Ser. No. 55,810, filed July 17, 1970 and now abandoned.

FIELD OF THE INVENTION

This invention relates to new processes for microbiological synthesis and particularly to such processes for the production of proteinaceous material employing a feedstock comprising a supporting medium and normally gaseous hydrocarbon substrate. More particularly the invention relates to such processes employing a fungus identified as a *Graphium* species.

REVIEW OF THE PRIOR ART

The bio-oxidation of normally gaseous hydrocarbons, particularly methane and ethane, by bacteria is well known, and many bacteria have been reported to grow on these substrates, for example, *Pseudomonas methanica*, *Methanomonas methanooxidins*, *Pseudomonas methanitrificans*, *Mycobaterium* species, and others. Such processes usually are carried out in a suitable aqueous nutrient medium at a pH of about 6.5–7.3 into which the gaseous substrate is fed, and from which the resultant microbial tissue can be separated. These processes, when capable of producing an edible nutritious product, have several attractive features, for example, in that the feed-stock materials are widely available and at the present time are relatively inexpensive. Moreover, the gaseous nature of these feedstocks enables them to be obtained economically in a relatively pure state, reducing or avoiding entirely the possibility that the product will be contaminated and/or will require extensive purification to be edible and palatable.

Edible fungi themselves are well known and widely used as foods, and U.S. patent specification Ser. No. 3,151,038 issued 29th Sept. 1964 to William D. Gray is an example of the use of a fungus of the class *Fungi Imperfecti* (Deuteromycetes) in a microbiological process for the production of fungal tissue comprising edible protein, the fungus being cultured aerobically with a feedstock comprising s source of carbohydrate and nitrogen.

U.S. Pat. Ser. No. 3,418,208, issued 24th Dec. 1968 to V. F. Coty is directed to a method for growing microbes on hydrocarbons in order to obtain increased yield. Reference is made to the uses of gaseous hydrocarbons having one to four carbon atoms, but the teaching of the patent is toward the removal of inhibiting compounds from the fermentation broth. The specification refers to a large number of micro-organisms but neither *Graphium* nor any of its synonyms are named. Significantly, the specific examples of the patent do not show any fungi growing on low molecular weight hydrocarbon substrates.

None of the prior art known to the applicants shows any fungi of the same family (Stilbacea) growing well on hydrocarbons.

DEFINITION OF THE INVENTION

It is an object of the present invention to provide a new fermentation process for the selective cultivation of micro-organisms.

It is another object of the present invention to provide a new fermentation process for the microbiological synthesis of protein-containing material utilizing normally gaseous hydrocarbon as a source of carbon and energy and employing a fungus.

In accordance with a first aspect of the present invention there is provided a process for the cultivation in a fermentation vessel of a selected microbiological culture in a feedstock material comprising a liquid nutrient medium and an energy-providing substrate, the process including the steps of:

a. inoculating the feedstock material in the vessel with a mixture of microbiological cultures including the said selected culture and the cultures having lower growth rates on the substrate to initiate a corresponding fermentation process;

b. initially operating the fermentation process by removing from the vessel at a first lower replacement rate a quantity of the fermentation broth and adding at the same lower rate sufficient feedstock material to replace the quantity of removed broth so as to maintain the quantity of feedstock in the vessel substantially constant;

c. thereafter increasing the replacement rate to a higher value rate sufficient to remove from the vessel cultures of lower growth rate than that of the said selected culture;

d. continuing the process at not less than the last mentioned rate until the said lower growth rate cultures have been effectively removed from the vessel, and e. then continuing the process for cultivation of the selected culture.

Also in accordance with the present invention there is provided a new process for the microbiological synthesis of protein-containing material comprising the steps of cultivating aerobically in a feedstock comprising a supporting medium and a normally gaseous hydrocarbon substrate selected from methane, ethane, propane, butane and mixtures of two or more such hydrocarbons a protein-producing fungus of Graphium species, and obtaining the synthesized protein-containing material from the resulting fermentation broth.

There is at the present time a constant search for new microbiological agents for various fermentation processes, and especially for such agents that will produce nutritious palatable protein or proteinaceous (i.e. protein-containing) material from inexpensive and readily available feedstocks. Although as described above proteinaceous materials have been produced using gaseous hydrocarbon by use of bacterial agents, it is believed that the processes particularly described and claimed in the present application are the first to successfully employ a fungus as the principal microbiological agent. Apart from the economics of any commercial process employing a fungus, such a system has a psychological advantage in that fungi are already widely regarded as complete acceptable foods, indeed in many cases as gourmet items, and accordingly the product of such a process is more readily acceptable for animal or human consumption. It is also believed from tests already undertaken with the products of these processes that, owing to the fungal nature of the principal agent, the resulting proteinaceous material is more readily digestible than those produced by exclusively bacterial processes.

Previously known bacterial processes for making protein from natural gas have not been widely adopted, largely for economic reasons. The first step in such conversion of low molecular weight hydrocarbons to single cell proteins is oxidation of the hydrocarbon to the corresponding alkanol. This step is thermodynamically difficult and rate limiting on the process. Workers have therefore chosen to use the alkanol as the starting material rather than the hydrocarbon. This problem does not arise in the process of the invention. Also, it has been found that the proteinaceous product of the bacterial process has very tough cell walls, so that breaking the cell walls to remove the new nucleic acid from the product and render the product fully edible is a difficult operation. The proteinaceous product made by the process of the invention has a much weaker cell wall. It is not in all cases of products of the present invention necessary to remove nucleic acid, but even when it is, the removal operation is much simpler and easier than with the bacterially produced proteinaceous material.

DESCRIPTION OF THE DRAWINGS

Particular preferred embodiments of the invention will now be described, by way of example with reference to the accompanying diagrammatic drawings, wherein.

DESCRIPTION OF THE PREFERRED EMBODIMENTS

In a preliminary process, a selected microbiological culture was cultivated in a feedstock material comprising a liquid nutrient medium and an energy providing substrate. The energy providing substrate was a mixture of natural gas and air. The nutrient medium consisted of the following, in aqueous solution, on a weight to volume basis of the water:

| | |
|---|---|
| Ammonium sulphate $(NH_4)_2SO_4$ | 0.1% |
| Potassium hydrogen orthophosphate $K_2H\ PO_4$ | 0.1% |
| Magnesium sulphate $MgSO_4.7H_2O$ | 0.05% |
| Calcium chloride $CaCl_2$ | 0.01% |
| Sodium chloride NaCl | 0.01% |
| Ferrou sulphate $FeSo_4.7H_2O$ | 0.0001% |

Ten liters of this medium had its pH adjusted to about 5.0 with hydrochloric acid and was placed in a suitable fermentation container.

The microbiological inoculum used was a mixture of microbiological cultures containing at least one specific culture capable of producing proteinaceous material from gaseous hydrocarbons as contained in the natural gas used as the energy providing substrate. Specifically, the inoculum consisted of raw sewage from Greenway Pollution Control Center, London, Ontario, Canada. About 5% by volume of microbiological inoculum was added to the nutrient.

The energy providing gaseous substrate consisted of a mixture of 40% natural gas and 60% air (V/V), the natural gas having as a typical analysis:

| | |
|---|---|
| Methane $CH_4$ | 90.5% |
| Ethane $C_2H_6$ | 6.0% |
| Nitrogen $N_2$ | 3.0% |
| Carbon dioxide $CO_2$ | 0.25% |
| Propane $C_3H_8$ | 0.21% |
| Iso-butane; n-butane } Iso-pentane; n-pentane | traces |

This preliminary process in accordance with the present invention was conducted in order to cultivate, and subsequently isolate the fungus growing on the natural gas and producing proteinaceous material therefrom, from the mixture of microbiological cultures employed. This process was conducted by initially replacing fermentation broth in the fermentation vessel with fresh feedstock, keeping the total quantity of feedstock in the vessel substantially constant, at a first replacement rate, and then increasing this replacement rate. When the subsequent, higher replacement rate is used, the cultures of lower growth rate are gradually washed out of the fermentation broth, with consequent concentration of the selected, fast growth rate culture (s). By continuing this process at or not less than the subsequent replacement rate, the lower growth rate cultures are effectively removed from the vessel, and then the process can be continued and protein provided under appropriate conditions by the cultivation of the selected, high growth rate culture.

The specific process of this preliminary process will be best followed by a reference to the accompanying drawings.

Figure 1A:
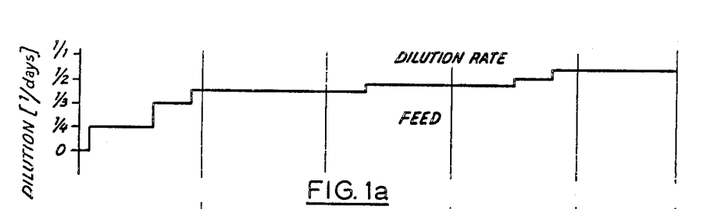
FIGS. 1a to 1d are graphs on a time ordinate in days showing the progress of an initial fermentation process, the respective abscissae consisting of the dilution rate of the fermentation broth, the pH of the nutrient feed material, the yield in milligrams per hour of dry tissue from broth withdrawn from the process, and the pH of the withdrawn broth.
Figure 1B:
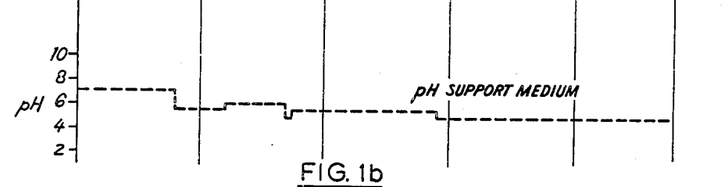
Figure 1C:
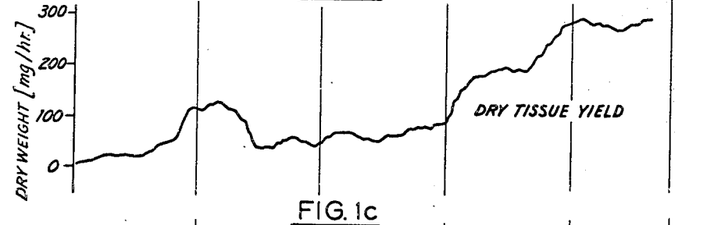
Figure 1D:
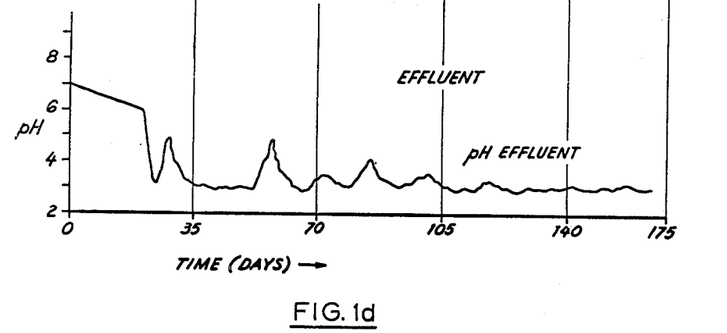

Referring now especially to FIGS. 1a to 1d, the system was agitated continuously by a stirrer at 150 r.p.m. and the temperature was maintained at 28° C ± 2° while the gaseous substrate was fed thereto at a rate of about 4 liters per minute; these conditions obtained for a period of about 3 days. On the fourth day new supporting medium liquid at a pH of about 7.0 was added with simultaneous withdrawal from the fermentation broth, so as to maintain the total volume (10) approximately constant while replacing 10 liters every 4 days to give a first replacement rate of ¼ days. The pH of the effluent broth (FIG. 1d) and the dry tissue yield therefrom (FIG. 1c) were both measured. An analysis of the dry tissue is given below.

At the end of 21 days the agitation by the stirrer was increased to 800 r.p.m. and the replacement rate was increased to a higher value, namely ⅓ days (replace whole volume of ten liters every 3 days). During this initial 21 day period using the first replacement rate, a mixed population of bacteria, protoza and fungi was observed, with the first two micro-organisms predominating; at 25 days the pH of the effluent broth was about 6.0 and the tissue yield about 11 mg/hour. At 28 days the pH of the supporting medium fed to the container was decreased to 5.5 and this change plus the increased dilution rate resulted in a sharp decrease in effluent broth pH to about 3.3, with an accompanying decrease in the bacterial and protozoa population, to the extent that the fungi became predominant. Thus, at this increased replacement rate, the lower growth rate cultures are gradually being removed, and are eventually essentially completely removed. An increase in the feed pH to 6.0 resulted in a sharp decrease in yield, and a further decrease of supporting medium feed pH to 5.0 was later found necessary to continue the new state, and this value was maintained thereafter, with the pH of the effluent broth stabilizing to a value between about 2.7 and 3.5. It will be seen from FIG. 1c that the formation of tissue increased markedly with each increase in dilution rate as the fermentation continued. The greater formation of tissue indicates the higher concentrations of selected, fast growth rate culture(s) in the broth and removal of lower growth rate cultures, until in the latter stages of the process, the selected culture(s) alone are being cultivated in the fermentation broth.

Two different fungi, and at least one bacterium, which were dominant in mixed culture in the fermentation medium were isolated by streaking the effluent on agar plates of the supporting medium and incubating the plates in enclosed dessicators supplied with 40% natural gas and 60% air. Hyphal tip isolations were taken from developing colonies. Pure cultures were obtained and stock cultures of these strains were maintained on the supporting medium, natural gas, and air. Sporulating stages of fungi were studied both in liquid media and on solid media in petri dishes and in slide cultures. Of the two fungi isolated, one grows on the supporting medium and natural gas, and cultures thereof grown upon carbohydrate still retain the ability to use natural gas for growth on subculture. This culture has been identified as a species of *Graphium*, the taxonomy thereof being given below. The bacterium has been identified as an acid tolerant species of *Pseudomonas methanica*. The second fungus has been identified as *Trichoderma viride* Link ex Fries and is not able to oxidize hydrocarbons in pure culture under the test conditions used, and is believed to use metabolites produced by the *Graphium* fungus and the bacterium.

EXAMPLE 1

This example illustrates the result of varying the percentage of inoculum added to laboratory scale fermentations carried out in 500 ml Erlenmeyer flasks, usually at a controlled temperature of 28° C ±2°. The flasks were agitated continuously on a rotary shaker at 200 r.p.m., being mounted within a closed environmental chamber whose atmosphere could be controlled. The flasks were fitted with cotton plugs and contained 100 ml of the supporting medium. A mixture of 40% natural gas and 60% air was fed continuously into the environmental chamber at a rate of about 2 liters per minute, so that it would perfuse into the flasks and the medium under zero pressure and upon demand of the fermentation process.

The broth inoculum containing isolated *Graphium* fungus was 7 days old; the flasks were inoculated in duplicate with respectively 1%, 2%, 3%, 4%, 6%, and 8% (V/V) of the broth and were incubated for 5 days. The dry weight of the resultant proteinaceous mycelium was determined by filtering a measured volume of broth using millipore filters and drying the filtered material overnight at 105° C. The results are shown in Table 1 below:

Table 1

| % inoculum (V/V) | dry wt. per 100 ml |
|---|---|
| 1% | 9.5 mg |
| 2% | 20.5 mg |
| 3% | 27 mg (average) |
| 4% | 27 mg (average) |
| 6% | 28 mg |
| 8% | 29 mg |

It will be seen that at 3% inoculum or above a maximum of about 27–28 mg dry weight of protein was obtained per 100 mg. broth, even with the relatively short incubation period of 5 days, illustrating the prolific growth and activity of the fungus in suitable but unoptimized conditions.

EXAMPLE 2

This example illustrates the result on the rate of oxidation of adjusting the initial pH of the nutrient medium in laboratory scale fermentations carried out as described for example I, but with constant supply of gas mixture to the individual flasks. The results are shown in Table 2 below. In each case the initial pH of the medium was adjusted with hydrochloric acid to the value shown and the flasks incubated for the same period of 5 days, whereupon the dry weight of mycelium (protein) produced was measured. The two series of flasks showed the same trend, but with some divergence in values. Both sets of values are therefore given.

Table 2

| Initial pH | Dry wt per 100 ml | |
|---|---|---|
|  | Series 1 | Series 2 |
| 2.5 | 0 | 0 |
| 3.5 | 13 | 23 |
| 4.5 | 33 | 62 |
| 5.5 | 25 | 42 |
| 6.5 | 27 | 58 |

These results show that substantially no growth occurs at 2.5 and the presence of an initial optimum point at 4.5. The sharp decrease at 5.5 is followed by an increase at 6.5 and clearly the pH range for growth under the conditions employed are at least from below 3.5 to 6.5 (say from 2.7) with at least an optimum at 4.5. This range can be widened by, for example, the use of a nitrate in the supporting medium as a source of nitrogen in place of the ammonium sulphate employed in this particular mineral salt medium, to a range of values such as 3.5–8.5.

EXAMPLE 3

This example shows with reference to Table 3 below the typical rate of protein synthesis in laboratory scale fermentations. The table also shows the effect of the progress of the process on the pH of the supporting medium. Two series of flasks were employed, in one of which the initial pH was adjusted to 4.5 and the second of which it was adjusted to 4.0, both sets being supplied continuously with the gaseous substrate fed into the flasks and the process being observed over a period of twelve days.

Table 3

| days | dry wt. yield mg/100 ml | pH (initial 4.5) | dry wt. yield mg/100 ml | pH (initial 4.0) |
|---|---|---|---|---|
| 1 | — | — | — | — |
| 2 | 5 | 3.9 | 5 | 3.7 |
| 3 | 11 | 3.5 | 21 | 3.3 |
| 4 | 30 | 3.2 | 30 | 3.2 |
| 5 | 32 | 3.1 | — | — |
| 6 | 36 | 3.0 | 33 | 2.9 |
| 7 | — | 2.9 | — | — |
| 8 | 42 | — | 38 | 2.8 |
| 9 | 38 | 2.8 | — | — |
| 10 | — | 2.8 | — | — |
| 11 | 38 | 2 | 37 | 2.8 |
| 12 | 38 | 2.9 | — | — |

Better growth was obtained with the higher initial pH of 4.5, but the same general growth response was obtained in both cases. If plotted the resultant curves are of typical sigmoid type with an initial lag phase of about 2 days at the beginning, followed by accelerated or exponential growth between 2 and 4 days when the rate of protein synthesis is 7.5 mg/liters ml hr. These lag and accelerated growth phases are accompanied by corresponding decreases in pH, the system initially at 4.5 dropping to 3.2, while the system initially at 4.0 dropped to 3.1. The stationary growth phase at the other end of the curve commenced at the end of about 4 days and thereafter there was only a minimal decrease in pH of both series.

For the highest rate of tissue formation it is desired to keep the pH of the supporting medium in the range 4.0–5.5. The lower values of pH are attractive in that the chance of secondary contaminating side reactions is lessened, and the two factors must be balanced with one another.

EXAMPLE 4

This example illustrates the effect of the composition of the gaseous hydrocarbon substrate on the process, and for this purpose gases of instrument grade purity (98% and above) were used in place of the commercially produced natural gas employed in the preceding examples. Closed flasks were employed and the required gaseous mixture metered in after evacuation. Each flask was inoculated with 5% of the Graphium culture with an initial pH of 4.5, and a gas chromatograph was used for analysis of the gaseous phase, employing columns of silica gel and/or molecular sieve 13X, (sold by Varian-Aerograph Ltd.), the gel giving good separation of methane, ethane and carbon dioxide, but with the air peak containing both oxygen and nitrogen. The results are given in table 4 below of analyses completed at 0, 5, 9, 15 and 20 days with the quantities of the gaseous constituents given in dimensionless units of peak area.

Table 4

| Gaseous Mixture %by Vol. | 0 | 5 | 9 | 15 | 20 | Terminal pH | Mycelium Dry wt. mg/100 ml |
|---|---|---|---|---|---|---|---|
| A | | Dimension-less units | | | | | |
| $CH_3CH_3$  50 | 126 | 128 | 123 | 109 | 105 | | |
| $CO_2$  0 | 0 | 3 | 5 | 53 | 60 | 3.4 | 18 |
| Air  50 | | | | | | | |
| B | | Dimension-less units | | | | | |
| $CH_4$  50 | 40 | 41 | 39 | 39 | 39 | | |
| $CO_2$  0 | 0 | 0 | 0 | 0 | 0 | 4.5 | 2.8 |
| Air  50 | | | | | | | |
| C | | Dimension-less units | | | | | |
| $CH_4$  50 | 40 | 41 | 39 | 39 | 39 | | |
| $CO_2$  0 | 0 | 0 | 0 | 0 | 0 | 4.5 | 2.8 |
| Air  50 | | | | | | | |
| C | | Dimension-less units | | | | | |
| $CH_4$  25 | 75 | 75 | 72 | 71 | 70 | | |
| $CH_3CH_3$  25 | 110 | 105 | 89 | 80 | 76 | | |
| $CO_2$  0 | 0 | 10 | 68 | 80 | 64 | 3.2 | 25 |
| Air  50 | | | | | | | |

In test A the flasks contained 50% ethane and 50% air and the utilisation of the ethane is demonstrated by its reduction in 20 days from 126 units to 105 units accompanied by the production of 18 mg/100 ml of protein and 60 units of carbon dioxide and accompanied by a drop in pH to 3.4.

In test B with methane and air no substantial oxidation was observed, with no apparent production of carbon dioxide of change in pH. The amount of mycelium present is not substially greater than that introduced by the inoculum. Nevertheless, as will be seen from test C above, methane is oxidised by the system, but the rate of reaction with methane alone is substantially slower under the conditions so far investigated.

Test C shows the results with flasks containing equal volumes of methane and ethane, and it will be seen that 34 units of ethane were utilized, together with 5 units of methane, with the production of 25 mg/100 ml mycelium protein and 64 units of carbon dioxide. These results may be contrasted directly with those of test A and show the synergism in the concurrent use of both hydrocarbons. It is not at present known how ethane influences the methane oxidation and could be an example of cooxidation or coutilization in which the *Graphium* fungus more readily oxidises methane in the presence of an exogenous substance such as ethane. It is also not known whether the oxidised methane is used directly as a source of energy and carbon, or is cooxidized with the ethane. However, the experiments definitely show that a mixture of methane and ethane gives improved growth and yield of *Graphium* over ethane alone with utilisation of methane. The exact mechanism can only be determined by experiments using methane or ethane labelled with $C_{14}$.

Since commercial natural gas consists principally of methane with much smaller proportions of ethane (6.0% typically from the source normally employed in these experiments) this synergistic effect is particularly important in the maximum efficient utilisation of the fungus for synthesis. For example, the gas mixture can be fed to the reactor under conditions which will completely utilize the available ethane and as much as possible of the accompanying methane, and the residual methane is then re-cycled with addition of ethane from some other source to continue the process. Such recycling has been tested under laboratory conditions and is found to be completely practical and feasible. In other processes the methane may be only partially re-cycled while the remaining fraction is exhausted and used for its heat value in other combustion processes. In still further processes, suitable gaseous feedstock material for use in the present invention may be made by a microbiological production. For example, bacteria are known which feed upon organic wastes and produce methane and/or other gaseous hydrocarbons. The methane or other gaseous hydrocarbons can then be isolated and used either alone or in admixture with natural gas or other sources of gaseous hydrocarbons, in connection with the graphium species in a fermentation process according to the present invention to produce proteinaceous material. In this way, an integrated process can be established for the microbiological conversion of organic waste material to edible proteinaceous material, using bacteria followed by graphium species, in accordance with this invention.

If desired, this microbiological process for the production of suitable gaseous substrates, such as the microbiological production of the gaseous hydrocarbon from sewage, can be designed so that there is produced as nearly as possible directly the optimum mixture of methane and ethane, which thereafter is used in processes in accordance with this invention.

The growth of the *Graphium* fungus on gaseous hydrocarbons of higher molecular weight was also tested in this experiment and the results of these tests are given in table 5 attached, the initial pH being 4.5 and the incubation period 10 days.

Table 5

| Gas Mixture | % Composition (v/v) | | | |
|---|---|---|---|---|
| Propane: | 25% | 50% | 75% | 0 |
| Air: | 75 | 50 | 25 | 100 |
| Mycelium $\left[\frac{mg}{100\ ml}\right]$ | 31 | 22 | 13 | 3 (inoculum) |
| Butane: | 25% | 50% | 75% | 0 |
| Air: | 75 | 50 | 25 | 100 |
| Mycelium $\left[\frac{mg}{100\ ml}\right]$ | 3 | 24 | 16 | 3 (inoculum) |

It will be seen that both propane and butane are utilized as a source of carbon and energy; tests carried out using higher molecular weight hydrocarbons than $C_4$ show no appreciable growth under the conditions so far employed. It will be seen that at 50% air/50% propane the mycelium yield was 22 mg/100 ml compared with 18 mg/100 ml for ethane, while the corresponding figure for butane was 24 mg/100 ml; the higher yield of 31 mg/100 ml for 25% propane/75% air will also be noted compared with the drastic reduction for butane. These higher weight yield figures are to be expected with substrates of higher molecular weight and are in commercial practice offset by the much lower incidence of propane (0.21%) and butane (traces only) in commercial supplies of natural gas.

EXAMPLE 5

This example illustrates particularly the result of varying the percentage of oxygen present in the gaseous substrate, and therefore available to take part in the oxidation accompanying these fermentation processes, and is directed to the determination of the mixture giving the highest utilisation of ethane. The effect of variation of the oxygen content with propane and butane are also illustrated by Table 5 in example 4 above.

Table 6 below shows the results of two sets of tests in which respectively 10% and 20% by volume was used in the flasks, each with 50%, 40% and 30% of oxygen and the balance nitrogen. The initial pH of the supporting medium was 4.5 and the fermentation was carried out for 16 days.

Table 6

| % $O_2$ by Vol. | % $N_2$ by Vol. | % $CH_3CH_3$ by Vol. | % $CO_2$ Produced | % Utilization of Ethane |
|---|---|---|---|---|
| 50 | 40 | 10 | 10 | 91 |
| 40 | 50 | 10 | 6.4 | 28 |
| 30 | 60 | 10 | 0 | 0 |
| 50 | 30 | 20 | 4 | 57 |
| 40 | 40 | 20 | 3 | 8 |
| 30 | 50 | 20 | 0 | 0 |

It will be seen that with 50% oxygen and 10% ethane a 91% depletion of the ethane was obtained, but a depletion of only 57% ethane occurred with the same amount of oxygen and 20% ethane, showing an effect on the reaction, which may be a limiting effect of the oxygen illustrated by Table 7 below. A sharp drop in utilisation occurred in both series with the reduction to 40% oxygen, while the reduction to 30% oxygen appeared to inhibit the reaction completely.

The preferred ratio of oxygen to ethane in particular fermentation processes has been investigated further and the results are given below in Table 7. In three series of tests with oxygen levels respectively of 10%, 20% and 50% the ethane concentration was adjusted to values of 5%, 15%, 25%, 35%, 45% and 60% (V/V) with the results shown.

Table 7

| | Dry wt. yield mycellium mg/100 ml | | |
|---|---|---|---|
| % ethane | 10% $O_2$ | 20% $O_2$ | 50% $O_2$ |
| 5 | 22 | 14 | 25 |
| 15 | 32 | 33 | 13 |
| 25 | 35 | 28 | 4 |
| 35 | 21 | 29 | 9 |
| 45 | 35 | 35 | 38 |
| 60 | 33 | 39 | 16 |

With 10% oxygen the rate of protein synthesis increases to a maximum at about 20–25% ethane, decreases to a minimum at about 35% and increases to another maximum at about 50%, a relatively high yield being obtained at all values of ethane tested. It must be noted that the results of Tables 6 and 7 cannot be correlated directly in view of the different calculations employed for the oxygen/ethane ratio. It may also be noted that air has been found to be a completely satisfactory source of oxygen with no special cleaning thereof required before it is fed into the reaction vessel.

A similar pattern of growth is obtained with 20% oxygen as with 10%, with the same high general yield of proteinaceous mycelium, the maximum of 33 and 39 mg/100 ml occurring at 15% and 60% ethane respectively, and a high minimum of about 29 mg/100 ml occurring between 20% and 30% ethane.

A substantial change is noted with 50% oxygen and the highest yields were obtained with a relatively low ethane value of 5% or a much higher value of 45%, the former value showing complete depletion of the ethane owing to the low quantity available for oxidation. At ethane concentrations between 20–35% by volume the yield decreased abruptly to a very low value of less than 5 mg/100 ml. The minimum value of the tissue yield showed a tendency to shift towards the lower concentration of ethane with higher oxygen levels. Thus, at all three levels of oxygen there was an intermediate level of ethane over the range of ethane tested between 5 - 60% in which the growth of the Graphium fungus decreased. The reason for this is not oxygen toxicity alone, although the effect was much greater at 50% by volume of oxygen. The decrease cannot be attributed to limiting oxygen since all three curves show a general similarity, and it may be caused by product or feedback inhibition which is overcome and not observed at higher relative concentrations of ethane. It is also possible that it is caused by a mutual solubility effect of the two gases in the aqueous phase which limits access thereto by the fungus.

EXAMPLE 6

It will have been observed from the preceeding examples that carbon dioxide is a normal by-product of the fermentation reactions, and this example illustrates the effect of varying this particular component of the gaseous phase on the progress of the reactions. It is known for example that the oxidation of methane by Pseudomonas methanica is directly influenced by the presence of carbon dioxide, and the natural gas used as the energy carbon source contains an appreciable percentage (0.25%) of this constituent, as well as the air that normally is used as the source of oxygen, so that the initial fermentation reaction described above inevitably was exposed to this constituent.

To test the effect in laboratory fermentations closed ecological flasks containing 100 ml of supporting medium and 5% of *Graphium* inoculum had their pH adjusted to 4.5 and their atmosphere adjusted on a volume basis to consist of 20% ethane, 20% oxygen, different concentration of carbon dioxide and the balance of helium. Four series of tests were used, two employing ammonium sulphate in the supporting medium and two using instead sodium nitrate as the source of nitrogen: very little difference was observed in the results of using the two different media, although greater success was obtained using ammonium sulphate. It is found with ammonium sulphate that the pH decreases, while with sodium nitrate it increases, and in either case an appropriate control must be applied if it is to be kept steady. The results for the ammonium sulphate containing medium are given below in Table 8:

Table 8

| % $CO_2$ added | Yield mg/100 ml |
|---|---|
| 0.0 | 10 |
| 2.0 | 26 |
| 6.0 | 21 |
| 12.0 | 20 |
| 20.0 | 19 |
| 30.0 | 16 |

In the flasks in which no carbon dioxide was added little growth was observed over the period of the experiment, and it has also been observed in connection with the growth results of Table 3 that lack of this constituent in the early stages of the fermentation causes a prolongation of the initial lag phase. At all of the levels tested the yield was substantially greater with a pronounced peak observed in flasks adjusted initially to 2.0% and 6.0% carbon dioxide. The effect of the carbon dioxide on the reactions does not appear to be related to the effect which its presence in the feedstock has on the pH of the supporting medium.

EXAMPLE 7

The purpose of this example is to show the results of adding additional growth factors, such as beef or yeast extract, to the supporting medium. The action of such additions is believed to be that it provides in an economic manner proteinaceous material, amino acids, enzymes and growth-supporting substances (such as vitamins, coenzymes) which can be utilized by the *Graphium* fungus and the other microbiological agents in their fermentation synthesis of the mycelium protein. The experiments show that the addition of these extracts to the mineral salts medium does result in a worthwhile increase in oxidation of the natural gas and consequent mycelium yield.

For full evaluation of the effect, series of tests were carried out with and without the natural gas substrate. The tests without extract and natural gas served as basic controls, while the tests with extract and without natural gas served as controls to determine the effect of the extract alone. The yield in the presence of extract and natural gas is designated $G_{NG}^i$, in the presence of extract and air $G_a^i$, the index $i$ indicating the percentage of extract added. The yield in the presence of natural gas and air without extract is designated $G_{NG}$ and the true number fold relative increase of synthesis I is then given by the relation $$I = \frac{G_{NG}^i - G_A^i}{G_{NG}}$$

The addition of 0.1% beef extract and no natural gas gave a yield of 16 mg/100 ml, while the average yield without extract and with natural gas was about 37 mg/100 ml. The yield with both natural gas and extract was 83 mg/100 ml which is approximately a two-fold increase.

Approximately the same quantity of yeast extract gave approximately a four-fold relative increase in synthesis. Yeast extract was found to be far more effective either with or without natural gas present, probably due to the fact that the fungoid nature of yeast ensures that the enzymes etc. present are more readily utilizable by the *Graphium*. A more detailed series of tests were therefore carried out using different percentages of yeast extract, and the results are given in Table 9 below. As in the preceding experiments the initial pH value was adjusted to 4.5 and the fermentation was allowed to proceed for five days.

Table 9

| % extract added | Relative Yield increase (fold) |
|---|---|
| 0.0 | |
| 0.1 | 2.0 |
| 0.2 | 3.4 |
| 0.3 | 4.5 |
| 0.4 | 5.9 |
| 0.8 | 5.5 |
| 1.5 | 1.8 |
| 2.5 | −3.8 |

It will be seen that the highest yield increase was obtained with about 0.4% added extract and at this level $G_{NG}^{0.4} - G_A^{0.4}$ was 196 mg/100 ml. With the addition of 0.3 to 0.8 of extract the increase is always greater than 4.5 fold whereas above 0.8 the value of I begins to decrease sharply showing the onset of an inhibiting effect that is very marked at 2.5%. A minimum for addition is 0.02%.

Although a particular aqueous supporting medium has been employed in the examples described in detail above it will be apparent to those skilled in the art that many other suitable media may be employed provided they contain the products required for synthesis of protein containing material by the fungus. It is usually important to provide an adequate source of nitrogen and depletion of this factor must be avoided to prevent corresponding limitation of the fermentation. Although in the process described fresh aqueous supporting medium was added to replace the withdrawn broth it will be apparent to the skilled practitioner that replenishment of the minerals removed by the fermentation reaction may only be necessary, and these may be added to the broth after removal of the fungal tissue therefrom, the replenished broth being returned to the reaction vessel. Although many of the examples described above are the result of batch type experiments the processes in accordance with the invention can be operated on a continuous basis. Moreover, in many of the examples the fermentation processes employed involve axenic culture of the pure *Graphium* fungus in order to obtain clearly defined results. This type of culture does involve sterilisation of the medium. It will be seen, however, that excellent results are also obtained in a non-sterile mixed culture system, and this has obvious economic advantages in commercial operation. It has also been noted in a general comparison of the production of mycelium by the pure *Graphium* fungus and the mixed culture that there is an observable increase of about 5% with the latter, showing that the other agents of the mixed culture are adding their own production and effectively are not competitively replacing the products of the *Graphium*.

The usual range of temperature for the fermentations is about 20°-38° C, with the preferred range 2820 -32° C.

EXAMPLE 8

A nutrient medium fed with natural gas as the energy-providing substrate was inoculated with a mixture of microbiological cultures containing at least one selected culture capable of growth in the medium with formation of proteinaceous material from the natural gas, at a relatively fast growth rate. The selection process was conducted with continuous replacement of fermentation broth with feedstock at a first initial rate and then at a subsequent higher value rate.

The nutrient medium and composition of the natural gas was as detailed in the foregoing preliminary process. The inoculum was 5% by volume of raw sewage. For the initial 10 days, the process was conducted at a replacement rate of 10 days (i.e. replace the whole volume of fermentation mixture once every 10 days) and the pH of the feed was 6.5. Then the replacement rate was increased to 4.7 days and the pH of the feed changed to 5.5. After operation for 2 weeks the pH stabilized between 3.5 and 3.8. At this dilution or replacement rate, cultures of low growth rate on the hydrocarbon substrate were removed. The process was continued for a total of six weeks, during the latter stages of which the medium contained only the selected cultures of high growth rates.

Prior to termination of the process, samples of the broth were extracted for isolating and identifying the cultures present. The cultivation media for isolating and identifying cultures was Coty's agar placed in incubators gased with controlled mixtures of methane, ethane and oxygen. Thus, by this means, cultivation of the selected culture(s) was continued in a process outside the original fermentation vessel as well as inside, after the dilution process had effectively removed the low growth rate cultures of the original fermentation broth.

Twelve cultures were isolated which grew upon natural gas and a mineral salts medium. All were fungal cultures. Four were identified as *Graphium* species. A second group of five cultures isolated, which grew on the same substrate and produced a different type of proteinaceous material (yellow, flat, powedery colonies with sparse aerial mycelium) were identified as species of *Acremonium*. A third group of three cultures produced a proteinaceous material which was compact olive grey with dense aerial mycelium. These were identified as *Phialophora jeanselmei* (*Torula jeanselmei*).

Composition of Proteinaceous Material

The product synthesized by the fermentation reaction, referred to herein variously as mycelium, tissue, fungal tissue, proteinaceous and protein-containing material may be separated from the broth by any suitable method such as centrifuging, in addition to the filtration specifically described herein. The physical appearance of the material depends essentially upon the method used for its extraction and typically is of yellow-greenish colour. This product may be used directly as a source of protein or it may be separated into fractions by removal of the fats, oils, carbohydrates etc. therefrom e.g. by solvent extraction techniques. The final dried protein fraction is found to be edible and palatable to human beings with no discernable objectionable odour, the taste being described as "mushroom-like" and attributed to the lipid content. The following example 8 given by Table 10 shows the results of analyses carried out on the products of the different substrates. The percentages in the table are by weight of the crude protein.

Typical values for protein content of the product of pure culture fermentation are from 46 to 51% of dry tissue weight. The freeze dried product possessed a general composition of 7.4–8.1% nitrogen, 9–11% lipids, 10–12% ash and the balance of dry weight of carbohydrates and fibrous material.

TABLE 10

| AMINO ACIDS | Natural Gas Substrate | Ethane Substrate | Range |
| --- | --- | --- | --- |
| Essential | | | |
| Arginine | 5.5 | 5.3 | 5.0 – 6.0 |
| Histidine | 2.5 | 3.3 | 2.0 – 3.5 |
| Iso-leucine | 5.1 | 4.0 | 3.5 – 5.5 |
| Leucine | 8.1 | 6.0 | 5.5 – 8.5 |
| Lysine | 8.5 | 7.7 | 7.5 – 9.0 |
| Methionine | 1.8 | 1.0 | 1.0 – 2.0 |
| Phenylalanine | 4.6 | 3.6 | 3.0 – 5.0 |
| Threonine | 1.7 | 3.9 | 1.5 – 4.5 |
| Tryptophan | 1.8 | 1.6 | 1.0 – 2.0 |
| Valine | 6.6 | 5.5 | 5.0 – 7.0 |
| Non-essential | | | |
| Alanine | 6.7 | 6.2 | 6.0 – 7.0 |
| Aspartic Acid | 11.5 | 7.1 | 6.0 – 12.0 |
| Cystine | 0.25 | | |
| Glycine | 6.5 | 5.8 | 5.0 – 7.0 |
| Glutamic Acid | 14.0 | 11 | 10.0 – 15.0 |
| Proline | 4.7 | 4 | 3.5 – 5.0 |
| Serine | 0.35 | 3.5 | |
| Tyrosine | 2.2 | 3.6 | 2.0 – 4.0 |

Preliminary toxicity and Nutritional evaluation

Although yeast and other fungal products have been consumed by man for years, in view of the unusual nature of the fungal single-cell protein derived from the processes of this invention the product was subjected to preliminary toxicological and nutritional tests. These tests were directed towards determining acute toxic responses, if any, rather than towards investigation of chronic problems. Young albino rats were used and short term screening tests both for obvious ill-effect and for the preliminary assessment of the nutritive value of the protein product were carried out. The animals were observed for effects on growth, food consumption, efficiency of food utilization, physical appearance and behaviour such as changes in posture or locomotion, appearance of excreta, etc.

Two tests were conducted, one of short-term for six days and the other longer term, when the rats were kept on the specific diet for 5 months. In the first test, involving 7 pairs of rats, with each pair fed a different amount of the *Graphium* biomass from 0% (control) to 100% of the available protein, no toxic effects were observed, even in animals fed solely on the *Graphium* biomass. They lost weight slightly over the six-day period but did not show any ill signs, no abnormalities being observed on autopsy. The longer term test, involving three groups each of six animals, with respectively 0%, 20% and 40% biomass in the diet as the protein source, also did not reveal any deleterious or toxic effects upon the animals. The weight gain of the group living on 40% biomass in their diet as a sole protein source was, however, slightly lower as compared to the central group on a casein diet. In all experiments as the amount of biomass in the ration increased the weight gain decreased and less of the ration was actually consumed. It was not possible to determine whether the decrease was nutritionally based or just from the lack of eating. Thus, the freeze dried biomass was not processed prior to ration preparation and this could have contributed to its lower consumption by the animals due to certain flavour and odour components present.

Brief Taxonomic Description of the "Graphium"Culture

The fungus was purified and in culture the isolate was found to produce two conidial states —monomematous and synnematous. The smooth walled one-celled conidia (2.5–5.6 ×4.9–9.0$\mu$) develop in the following ways:

The synnematous state

An erect column of parallel hyphae branches at the apex to form a fan of sporogenous annellophores. Each sporogenous hypha produces a single apical conidium which readily separates from the parent hypha. Elongation of the annellophore and successive proliferation of further conidia through the apex occurs, resulting in the formation of node-like annellations on the sporogenous cell. The long-cylindric conidia, rounded at the distal end and truncate at the basal end, accumulate in a ball or "slime head" at the apex of the coremium. The synnematous state therefore resembles *Graphium* rather than *Doratomyces*. Under some conditions the synemmata have bulbous bases, therefore, the possibility remains that the culture isolated is *Graphium*

The monomematous state

Annelophores were formed at the apex of single hyphae in a similar manner to that described above for the synnematous state. This monomematous conidial form is a modified *Scopulariopsis* in which the spores separate from the parent hypha and from one another thus forming "spore balls". Sometimes in slide culture the conidia do not separate but remain in a chain as is common in *Scopulariopsis*. Another type of conidial development occurred when the conidiophore renewed growth by sympodial extension just behind the terminal annellophore rather than by proliferation through the cross wall of terminal annellophore. The conidium produced on the short symodial swelling is also an annelophore. The sympodial type of development resembles the popular concept of *Sporotrichum*. However, there is confusion in the literature surrounding the relationship of *Sporotrichum*, *Sporothrix* and *Chrysosporium*. The unknown isolate has clavate aleuriospores (=annellophores) with a truncate base bearing an annular frill a diagnostic feature of *Chrysosporium;* the smooth wall is also more characteristic of *Chrysosporium* than Sporotrichum which usually has rough walled aleuriospores. In its sympodial form it resembles *Sporothrix* and *Sporothrichum*. The plasticity of this isolate cuts across previously erected boundaries and since no perfect stage has been produced, a detailed comparative study is necessary before a complete identification can be made.

For convenience in terminology in the preparation of this specification the fungus has been referred to throughout as a species of *Graphium*. For a more detailed review of the taxonomy of the mixed culture reference may be made to our publication entitled "Growth of Graphium Species on Natural Gas" published in the Canadian Journal of Microbiology of October 1969. (Volume 15, page 123, et seq).

In fullfillment of the requirements of 35USC112 a viable sample of the culture was deposited prior to the filing of application No. 55,810 in the Culture Collection of the Department of Botany, University of Western Ontario, London 72, Ontario, Canada, under registration number UWO 27. Samples of the culture will be available to the public upon grant of Letters Patent on the present application.

Other viable samples of the culture have been deposited subsequent to the filing of application No. 55,810 with the Northern Regional Research Laboratory, Peoria, IL., U.S.A., and given culture number NRRL 3915, and at the U.S. Army Natick Laboratories, Natick, Mass. U.S.A. under Q.M. 9375.

Other closely related *Graphium* strains or mutants may be employed in processes in accordance with the invention. Thus, in addition, the applicants have found the following genera containing cultures which are identical or similar in taxonomic relation to the original culture and may eventually be reclassified in that genus. Thus, many of these genera contain species which grow upon ethane and natural gas as a sole source of carbon and energy. These genera are:

1. Phialophora species *Phialophora jeanselmei* (*Torula jeanselmei*)
2. *Acremonium species Acremonium sensu*
3. *Cephalosporium* species
4. *Rhinocladiella mansonii* 5. *Cladosporium* species However, no species have as yet been isolated which exhibit as efficient a growth as that described in detail above.

We claim:

1. A process for the microbiological preparation of protein containing material comprising cultivating aerobically a protein producing species of Graphium fungus having all the characteristics of Graphium UWO 27 in a fermentation medium containing a nitrogen source and a hydrocarbon substrate selected from the group consisting of methane, ethane, propane, butane and mixtures of two or more of said hydrocarbons and separating the protein containing material from the fermentation medium.

2. A process for the microbiological preparation of protein containing material comprising cultivating aerobically a protein producing species of *Graphium* fungus in a fermentation medium which comprises a liquid, nitrogen containing nutrient and a hydrocarbon substrate selected from the group consisting of methane, ethane, propane, butane and mixtures of two or more of said hydrocarbons, wherein said protein producing species of Graphium fungus is obtained from a mixture of microbiological cultures by replenishing the medium in which the cultivation of said mixtures of cultures is being effected at increasing rates to effectively remove there from the slower growing microorganisms of said mixture thereby to select said protein producing species of Graphium and separating the protein containing material from the fermentation medium.

3. A process for the microbiological synthesis of protein containing material in which at least one faster growing microbiological culture selected from the group consisting of protein producing fungus of Graphium, acid tolerant bacterium of Pseudomonas methanica and mixtures thereof are cultivated in a liquid nutrient medium containing a hydrocarbon substrate selected from the group consisting of methane, ethane, propane, butane and mixtures of two or more of said hydrocarbons, the process including the steps of:
 a. inoculating the nutrient medium with a mixture of microbiological cultures including said faster growing culture and cultures having lower growth rates on the substrate to initate a fermentation process,
 b. initially operating the fermentation process by removing a vessel at a first lower replacement rate a quantity of the fermentation medium and adding at the same lower rate sufficient liquid nutrient medium to replace the quantity of removed medium so as to maintain the quantity of medium in the vessel substantially constant,
 c. thereafter increasing the replacement rate to a higher rate sufficient to remove from the vessel, cultures of lower growth rate than that of said faster growing culture,
 d. continuing the process at not less than said increased replacement rate until said lower growth rate cultures have been effectively removed from the vessel, and
 e. then continuing the process for cultivation of the faster growing culture.

4. A process as claimed in claim 3, wherein said faster growing culture is the protein producing fungus of Graphium species having all the characteristics of Graphium UW0 27.

5. A process as claimed in claim 3, wherein the said faster growing culture is an acid-tolerant bacterium of species Pseudomonas methanica.

6. A process as claimed in claim 3, wherein the said faster growing culture is a protein producing fungus of Graphium species together with an acid-tolerant bacterium of species Pseudomonas methanica.

7. A process as claimed in claim 3, wherein the said faster growing culture is a protein producing fungus of Graphium species having all the characteristics of Graphium UWO 27 together with an acid-tolerant bacterium of species Pseudomonas methanica.

8. A process as claimed in claim 3, wherein the said substrate is a mixture comprising ethane and methane.

9. A process as claimed in claim 8, wherein the said substrate is natural gas.

10. A process as claimed in claim 8, wherein the said substrate is a mixture of ethane and methane in which methane is the major component and including the step of withdrawing residual methane from the fermentation process, adding further ethane to the withdrawn residual gas, and returning the resultant mixture to the process.

11. A process as claimed in claim 3, wherein the culture medium has a pH in the range 2.7 to 8.5.

12. A process as claimed in claim 11, and including the addition to the culture medium of liquid nutrient of pH in the range of 3 to 6.5 to replace withdrawn medium.

13. A process as claimed in claim 11, wherein the culture medium comprises from 2 to 4% by volume of carbon dioxide.

14. A process as claimed in claim 3, wherein said substrate comprises ethane with not more than 50% by volume of oxygen.

15. A process as claimed in claim 14, wherein said substrate comprises ethane with not more than 20% by volume of oxygen.

16. A process as claimed in claim 3, wherein the culture medium comprises from 0.5 to 75 by volume of carbon dioxide.

17. A process as claimed in claim 3, wherein the culture medium comprises from 0.02 to 1.5% by volume of a growth supporting factor.

18. A process as claimed in claim 17, wherein the culture medium comprises from 0.02 to 1.5% by volume of yeast extract.

* * * * *